United States Patent [19]

Ono et al.

[11] Patent Number: 4,554,243

[45] Date of Patent: Nov. 19, 1985

[54] SILVER HALIDE MATERIAL WITH PHOTOGRAPHIC AGENT BLOCKED BY NUCLEOPHILIC ATTACK REMOVABLE GROUP

[75] Inventors: Mitsunori Ono; Isamu Itoh, both of Kanagawa, Japan

[73] Assignee: Fuji Photo Film Co., Ltd., Kanagawa, Japan

[21] Appl. No.: 613,986

[22] Filed: May 25, 1984

[30] Foreign Application Priority Data

May 25, 1983 [JP] Japan .................................. 58-92083

[51] Int. Cl.$^4$ .......................... G03C 1/40; G03C 1/34; G03C 1/42; G03C 1/10
[52] U.S. Cl. .................................. 430/543; 430/222; 430/223; 430/559; 430/561; 430/563; 430/566; 430/607; 430/611; 430/598; 430/614; 430/955; 430/957; 430/959; 430/960
[58] Field of Search ............... 430/222, 223, 955, 957, 430/959, 960, 563, 566, 607, 611, 614, 598, 543, 559, 561

[56] References Cited

U.S. PATENT DOCUMENTS

| | | | |
|---|---|---|---|
| 3,980,479 | 9/1976 | Fields et al. | 430/222 |
| 4,139,379 | 2/1979 | Chasman et al. | 430/223 |
| 4,358,525 | 11/1982 | Mooberry et al. | 430/222 |
| 4,468,450 | 8/1984 | Meneghini et al. | 430/222 |
| 4,468,451 | 8/1984 | Foley | 430/222 |

*Primary Examiner*—Richard L. Schilling
*Attorney, Agent, or Firm*—Sughrue, Mion, Zinn, Macpeak, and Seas

[57] ABSTRACT

A silver halide photographic light-sensitive material is described which comprises a support having thereon a light-sensitive silver halide emulsion layer, wherein the photographic light-sensitive material therein contains a blocked photographic agent capable of releasing a photographically useful agent and the blocked photographic agent has a carbonyl group or thiocarbonyl group to which a hydrogen atom or a carbon atom is directly bonded and is substituted with a photographically useful group which is capable of being released upon an intramolecular nucleophilic attack by the oxygen atom in the carbonyl group or the sulfur atom in the thiocarbonyl group.

The precursor of photographic agent is completely stable during storage prior to use of the photographic light-sensitive material, and releases a photographic agent at a desired time upon the processing of the photographic light-sensitive material. The precursor also exhibits its function to a substantial degree in a relatively low pH range. A method of forming an image using the silver halide photographic light-sensitive material is also described.

36 Claims, No Drawings

SILVER HALIDE MATERIAL WITH PHOTOGRAPHIC AGENT BLOCKED BY NUCLEOPHILIC ATTACK REMOVABLE GROUP

FIELD OF THE INVENTION

The present invention relates to a photographic light-sensitive material and, more particularly, to a photographic light-sensitive material containing a precursor compound of a photographically useful agent in which the active group is blocked.

BACKGROUND OF THE INVENTION

Use of a photographically useful agent that has been previously incorporated in a photographic light-sensitive material and so contrived that its effect will be produced at the desired appropriate time involves various features different from those involved when using such an agent by addition to a processing solution. Specific examples of the features in the former case are as follows: The incorporation in a photographic light-sensitive material enables effective utilization of photographic agents of the kind which tend to decompose under the acid alkaline or oxidation reduction conditions, and consequently, can not withstand the long-term storage in a processing bath and at the same time, makes it possible to simplify the composition of a processing solution to be employed associated therewith, thereby facilitating the preparation of the processing solution. Further, this makes it possible to force a required photographic agent to function at a desired time during the photographic processing, or at only a desired place, that is, in only a specified layer and the neighboring layers of a multilayer photographic light-sensitive material. Furthermore, this permits the presence of a photographic agent in the photographic light-sensitive material in such an amount as to vary as a function of silver halide development. However, if a photographic agent is added to a photographic light-sensitive material in its active form, it becomes impossible to make the photographic agent exhibit its ability to the expected degree, because during storage before photographic processing it reacts with other components contained in the photographic light-sensitive material, or it is decomposed by heat, oxygen, etc. One method for solving the above-described problem involves adding a photographic agent to a photographic light-sensitive material in such a form that its active group is blocked and turned photographically inactive, that is, in a form of its precursor. Such a method can have various advantages in various cases to which it is applicable. For instance, in the case where the useful photographic agent is a dye, blocking a functional group of the dye which has a great effect on its spectral adsorption characteristic results in a shift of its spectral absorption band to shorter wavelengths or to longer wavelengths, and therefore, even if the dye is present in a silver halide emulsion layer having the spectral sensitivity in the wavelength region corresponding to the absorption band which the dye has in the unblocked state, a lowering of the sensitivity due to the so-called filter effect can be prevented. In another case, where the useful photographic agent is an antifoggant or a development restrainer, blocking of their active groups makes it possible to suppress desensitization arising from adsorption of these agents to light-sensitive silver halide grains and formation of silver salts upon storage and at the same time, release of these agents at required times permits the reduction of fog density without being attended by a decrease in the sensitivity, the prevention of fog due to overdevelopment, development stoppage at a desired time, and so on. In still another case, where the useful photographic agent is a developing agent, an auxiliary developing agent or a fogging agent, if their active or adsorptive groups are blocked, various photographically adverse effects which arise from semiquinones and oxidants produced by aerial oxidation upon storage can be prevented, and generation of fogging nuclei upon storage can also be prevented because injection of electrons into silver halide grains can be inhibited. Therefore, stable processing can be effected therein. In a further case that the useful photographic agent is a bleach accelerating agent or a bleach-fix accelerating agent, it becomes also possible to prevent reactions with other components copresent in the photographic light-sensitive material from occurring upon storage by blocking its active group and that, to make its expected ability bring into full play at a desired time by removing the blocking group.

As described above, a precursor of a photographic agent can be utilized as an extremely valuable tool in bringing out abilities of the photographic agent to the best advantage. However, the precursor must satisfy very severe requirements for the purpose of practical use. That is, it must be one which can satisfy two requirements contradictory to each other; one consists in ensuring stable presence of the precursor under storage conditions, and the other consists in setting its blocking group loose at a desired time during processing and in releasing the photographic agent rapidly and efficiently.

A number of techniques for blocking a photographic agent have already been known. For instance, a technique using a blocking group such as an acyl group, a sulfonyl group or the like is described in U.S. Pat. No. 3,615,617; a technique which utilizes such blocking groups as to release a photographic agent by the so-called reversal Michael reaction is described in U.S. Pat. Nos. 3,674,478, 3,791,830, and 4,009,029; a technique which utilizes such a blocking group as to release a photographic agent with the production of quinone methide or its analogs by intramolecular electron transfer is described in U.S. Pat. Nos. 3,674,478, 4,416,977, 4,420,554, and Japanese Patent Publication (unexamined) Nos. 1139/83 and 1140/83; a technique which utilizes an intramolecular ring-closing reaction is described in U.S. Pat. No. 4,310,612; a technique which utilizes cleavage of a 5-membered or 6-membered ring is described in U.S. Pat. Nos. 4,335,200 and 4,350,752, and Japanese Patent Publication (unexamined) No. 179842/82; and so on. However, these photographic agents blocked with known blocking groups suffer defects; for example, although stable under storage conditions, some precursors require a high alkaline condition such as pH higher than 12 for the processing because the photographic agent-releasing rate thereof is too slow; other precursors decompose gradually to cause a failure of its function when maintained under storage conditions, even though it can release the photographic agent at a sufficiently fast rate by the processing under mild conditions such as using a processing solution of the pH range 9 to 11; and so on.

SUMMARY OF THE INVENTION

An object of the present invention is, therefore, to provide a blocked photographic agent which is completely stable under storage conditions and which can release the photographic agent at a desired time during processing.

Another object of the present invention is to provide a blocked photographic agent which can be sufficiently unblocked even with a processing solution having a relatively low pH, such as in the pH range of 9 to 12.

Other objects of the present invention will become apparent from the following detailed description and examples.

These objects of the present invention are attained by a silver halide photographic light-sensitive material which comprises a support having thereon a light-sensitive silver halide emulsion layer, wherein the photographic light-sensitive material therein contains a blocked photographic agent capable of releasing a photographically useful agent and the blocked photographic agent has a carbonyl group or thiocarbonyl group to which a hydrogen atom or a carbon atom is directly bonded and is substituted with a photographically useful group which is capable of being released upon an intramolecular nucleophilic attack by the oxygen atom in the carbonyl group or the sulfur atom in the thiocarbonyl group.

DETAILED DESCRIPTION OF THE INVENTION

The photographically useful group may contain a timing group.

Preferred compounds of the blocked photographic agent according to the present invention can be represented by formula (I):

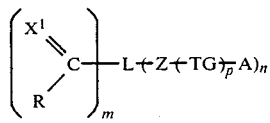
(I)

wherein $X^1$ represents an oxygen atom or a sulfur atom; Z represents an electrophilic group; A represents a photographically useful agent moiety; TG represents a timing group; L represents a linking group which is bonded to

through a carbon atom thereof; R represents a hydrogen atom or a substituent which is bonded through a carbon atom thereof; m and n each is an integer from 1 to 3, preferably an integer from 1 to 2; and p is 0 or 1.

In formula (I) above, A represents a photographically useful agent moiety. More specifically, suitable examples of the photographically useful agent which can be employed include anti-foggants or development restrainers represented by mercaptotetrazoles, mercaptotriazoles, mercaptobenzimidazoles, benzotriazoles, benzimidazoles, indazoles, etc.; developing agents represented by hydroquinones, aminophenols, p-phenylenediamines, etc.; auxiliary developing agents or development accelerators represented by pyrazolidones; fogging agents represented by hydrazines, hydrazides, acetylenes, tetrazolium salts, etc.; dyes represented by azo compounds; compounds possess such a redox function as to enable the release of photographically useful agents as described above as a function of silver halide development, for example, coloring materials for color diffusion transfer photographic materials, DIR (development inhibitor releasing) hydroquinones, etc.; and so on.

The moiety A may be bonded directly to the electrophilic group Z (when p=0) or may be bonded to the electrophilic group Z via a timing group (when p=1). Specific examples of usable timing groups include connecting groups such as a timing group which release A by an intermolecular ring-closing reaction, as described in Japanese Patent Publication (unexamined) No. 145135/79; a timing group which releases A through intramolecular electron transfer, as described in British Pat. No. 2,072,363, Japanese Patent Publication (unexamined) No. 154234/82, etc.: a timing group which releases A with the evolution of carbon dioxide, as described in Japanese Patent Publication (unexamined) No. 179842/82: a timing group (—OCH$_2$— group) which releases A with the evolution of formaldehyde: and so on.

Structural formulae of representative examples of the above-described timing groups (showing location of attachment to moiety A) are illustrated below.

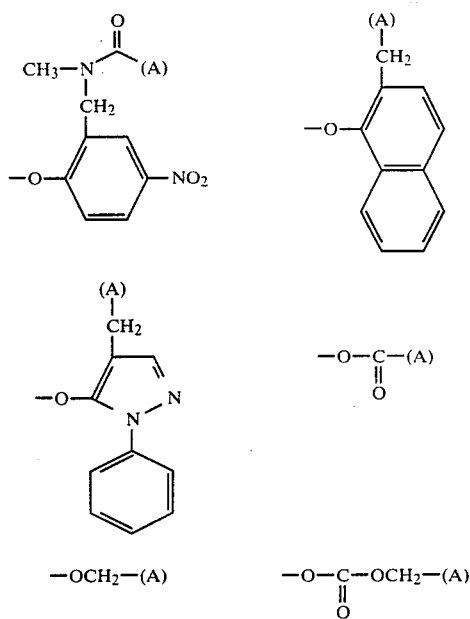

—OCH$_2$—(A)     —O—C—OCH$_2$—(A)

In formula (I) above, Z represents any electrophilic group. More preferably, Z represents a carbonyl group, a thiocarbonyl group, a sulfonyl group, a sulfinyl group, an allyl group or a benzyl group.

In formula (I) above, L represents a linking group which is bonded to $$R-\overset{X^1}{\underset{\|}{C}}-$$

through a carbon atom and preferably which is capable of forming a 5-membered to 7-membered ring upon a nucleophilic attack of $X^1$ to Z. Suitable examples of the linking groups include an alkylene group, an alkyloxyalkylene group, an alkylaminoalkylene group, an alkenylene group, an arylene group, a cyclocyclene group, a heterocyclene group, an alkyleneamino group, an alkenyleneamino group, an aryleneamino group, a cyclocycleneamino group, a heterocycleneamino group, etc., and combinations thereof.

In formula (I) above, R represents a hydrogen atom or a substituent which is bonded through a carbon atom thereof including, for example, an alkyl group, an alkenyl group, an aryl group, a cycloalkyl group or a heterocyclic group.

More preferred precursor compounds represented by formula (I) according to the present invention can be represented by general formula (II).

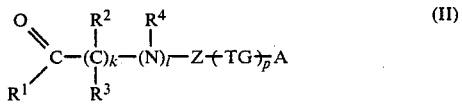

wherein A, TG, p, and Z each has the same meaning as defined therefor in formula (I); $R^1$ has the same meaning as defined for R in formula (I); $R^2$, $R^3$ and $R^4$ each represents a substituent; k is an integer from 1 to 4; l is 0 or 1; and the sum of k and l is from 2 to 4.

In formula (II) above, $R^2$ and $R^3$, which may be the same or different, each represents preferably a hydrogen atom, a halogen atom, an alkyl group, an alkenyl group, a phenyl group, a hydroxy group, an alkoxy group or an acyl group and these groups may have a substituent, $R^2$ and $R^3$ may together form a double bond or a ring, or the carbon atom substituted with $R^2$ and $R^3$ may form a cycloalkyl ring, an aryl ring or a heterocyclic ring when k is 2 to 4.

In formula (II) above, $R^4$ preferably represents an alkyl group, an alkenyl group or a phenyl group. $R^1$, $R^2$, $R^3$ and $R^4$ may bond each other to form a ring as far as the structure in which the oxygen atom of the carbonyl group can perform an intramolecular nucleophilic attack to Z is maintained.

Particularly preferred examples of $R^1$ include a hydrogen atom, an alkyl group having from 1 to 17 carbon atoms, an alkenyl group having from 3 to 17 carbon atoms, a phenyl group having from 6 to 21 carbon atoms and a heterocyclic group having from 4 to 21 carbon atoms. Particularly preferred examples of $R^2$ and $R^3$ include a hydrogen atom, a halogen atom and an alkyl group. A particularly preferred example of the ring which is formed with the carbon atom substituted with $R^2$ and $R^3$ is a phenyl group. Particularly preferred examples of $R^4$ include an alkyl group having from 1 to 10 carbon atoms and a phenyl group having from 6 to 21 carbon atoms. Particularly preferred examples of Z include a carbonyl group and a sulfonyl group. A particularly preferred integer for k is 1 to 3 and l is 1 when k is 1, l is 0 or 1 when k is 2 and l is 0 when k is 3. When k is 2 or 3,

may have structures different from each other.

Moiety A can be appropriately selected depending on photographic properties and releasing rate to be required. Particularly preferred results can be obtained when antifoggants represented by mercaptotetrazoles or benzotriazoles, auxiliary developing agent or development accelerators represented by pyrazolidones, or developing agents represented by p-phenylenediamines are selected.

It is very surprising that the precursor compounds according to the present invention are completely stable under storage conditions and can rapidly release the photographically useful agent at a desired time upon the processing. The mechanism by which these preferred results are achieved is not entirely clear, but it may be explained as follows. It is assumed that the release of a photographically useful agent occurs in the manner as shown in Scheme 1 below.

SCHEME 1

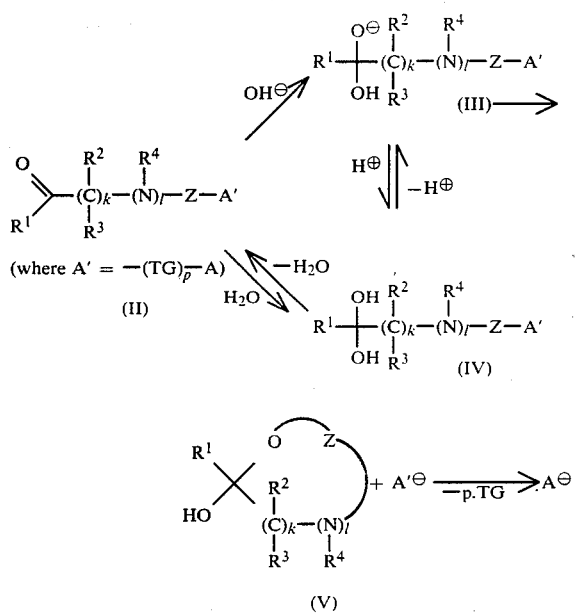

wherein A, Z, $R^1$, $R^2$, $R^3$, $R^4$, TG, k, l and p each has the same meaning as defined therefor in the above described formula (II).

With reference to Scheme 1, the stability of the precursor compound under storage conditions can be explained by means of an idea that at a low pH range of the storage conditions the compound (III) is hardly formed or, if formed, it is reacted with a proton to form the compound (IV) which can not release the photographically useful agent because of its low nucleophilicity. On the other hand, it is considered that the photographically useful agent is rapidly released upon the intramolecular nucleophilic reaction of the compound (III) since the equilibrium between the compound (III) and the compound (IV) formed is overwhelmingly inclined toward the compound (III) at a high pH condition of the processing.

However, the coexistence of the contradictory properties, i.e., stability under storage conditions but rapid release of the photographically useful agent during processing, of the precursor according to the present invention is difficult to explain only on the above described ground. It may be considered that the reactions as shown in Scheme 2 below occur.

SCHEME 2

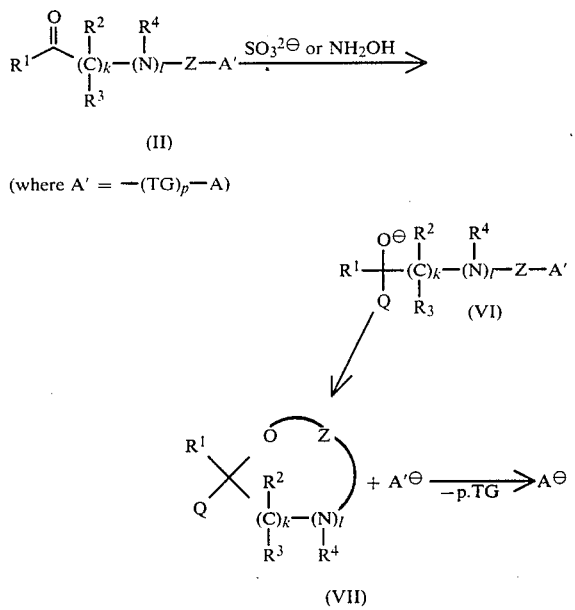

wherein A, Z, $R^1$, $R^2$, $R^3$, $R^4$, TG, k, l and p each has the same meaning as defined therefor in formula (II) described above, and Q represents

or —NHOH.

That is, in addition to the reaction of the compound (II) with a $OH^\ominus$ ion at the time of processing, it is considered that the carbonyl group of the compound (II) is attacked by a sulfite ion or hydroxylamine present in the processing solution to form the compound (VI) and the alcoholate anion of the compound (VI) attacks Z to form the compound (VII) and $A^\ominus$. In other words, the release of the photographically useful agent from the precursor according to the present invention is thought to be significantly accelerated with the sulfite ion or hydroxylamine present in the processing solution. Although the details of accelerating effects are not clear, in fact, such accelerating effects have been confirmed as a result of experiments in a solution system as illustrated in Example 1 hereinafter. Therefore, the greater effects of the present invention can be achieved by processing the photographic light-sensitive material containing the precursor according to the present invention with a processing solution containing a sulfite ion or hydroxylamine.

The amount of the precursor compound according to the present invention that is used can be varied depending on the kind of photographically useful agent involved. More specifically, in the case of the antifoggant of mercapto group-containing type, such as a mercaptotetrazole, etc., it ranges from $10^{-9}$ to $10^{-2}$ mole, and preferably from $10^{-6}$ mole to $10^{-3}$ mole, per mole of silver; in case of the antifoggant of azole type, such as a benzotriazole, etc., it ranges from $10^{-8}$ mole to $10^{-1}$ mole, and preferably from $10^{-5}$ mole to $10^{-2}$ mole, per mole of silver. In the case of a developing agent such as a p-phenylenediamine, or an auxiliary developing agent such as a pyrazolidone, it ranges from $10^{-4}$ to 10 moles, and preferably from $10^{-2}$ mole to 5 moles, per mole of silver.

Specific examples of the useful blocked photographic agents according to the present invention are set forth below, but the present invention should not be construed as being limited thereto.

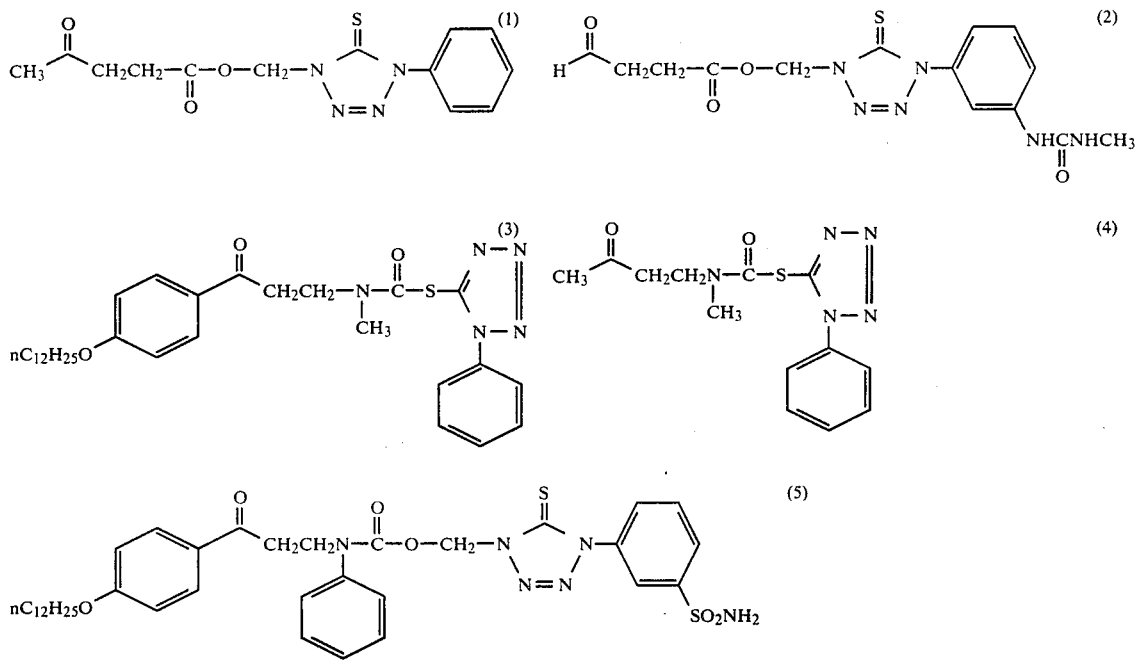

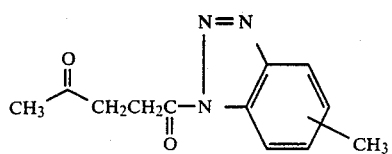 (6)
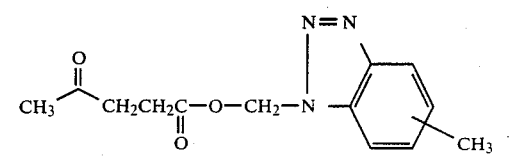 (7)
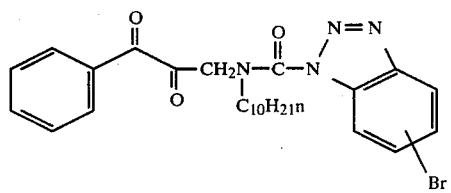 (8)
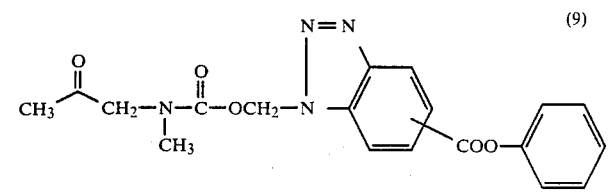 (9)
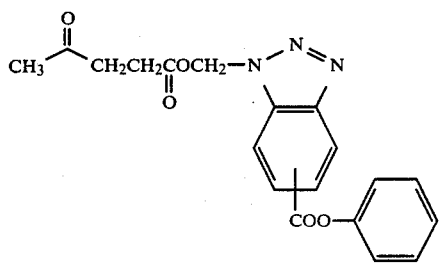 (10)
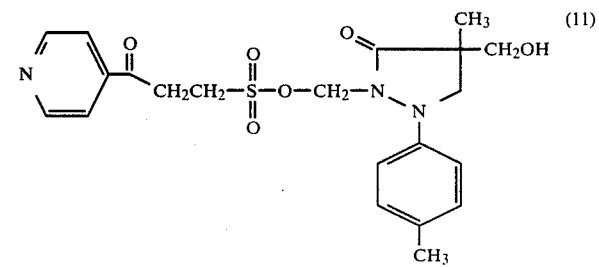 (11)
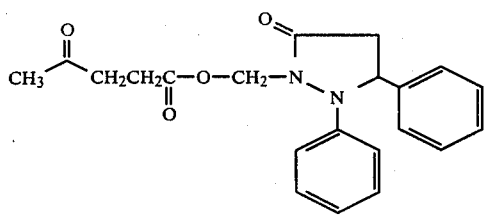 (12)
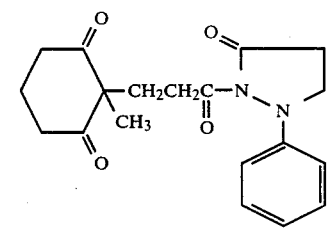 (13)
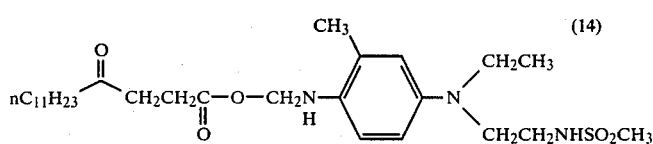 (14)
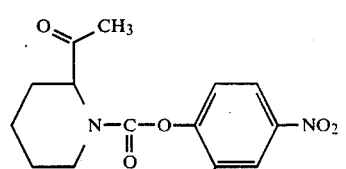 (15)
 (16)
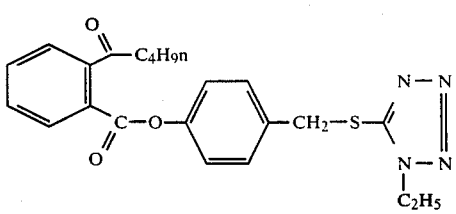 (17)

-continued
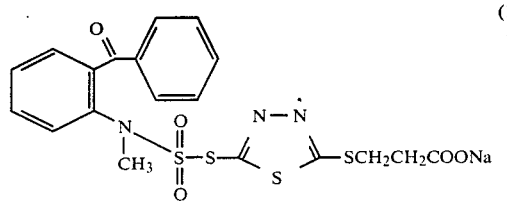 (18)
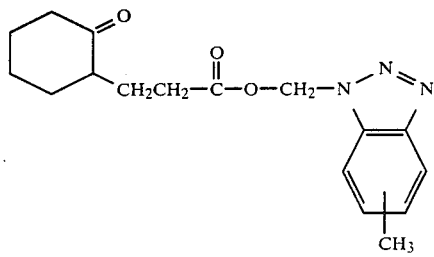 (19)
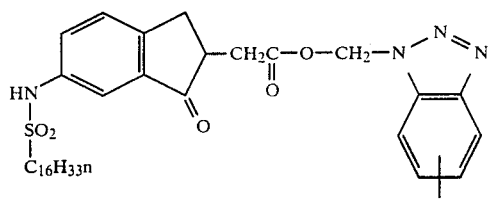 (20)
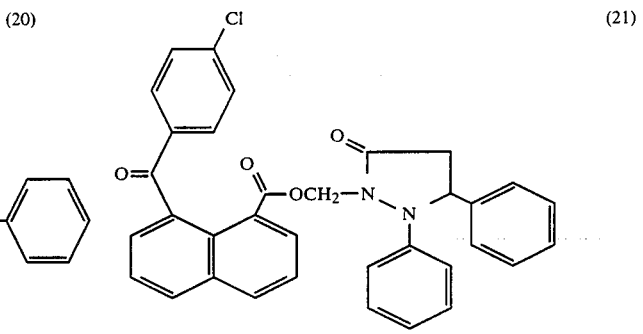 (21)
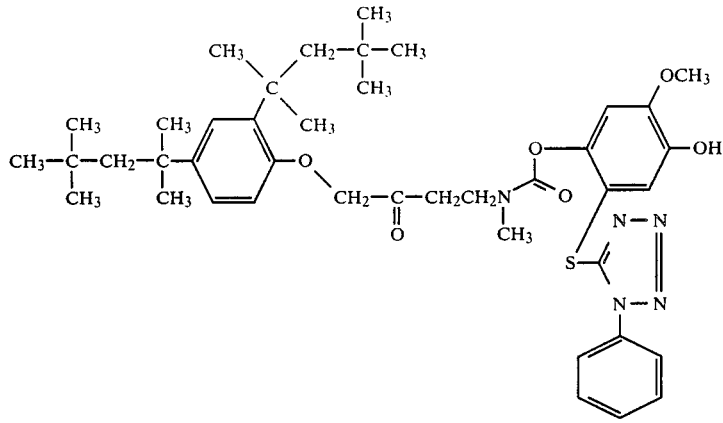 (22)
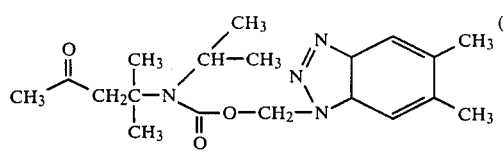 (23)
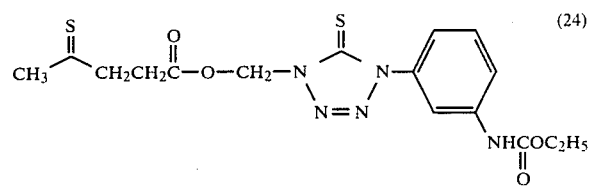 (24)
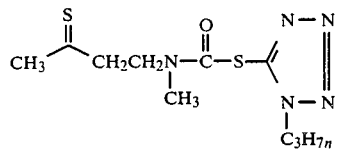 (25)
The precursor compounds according to the present invention can be easily synthesized using such general methods as illustrated by the following Reaction Schemes 3 and 4.
REACTION SCHEME 3

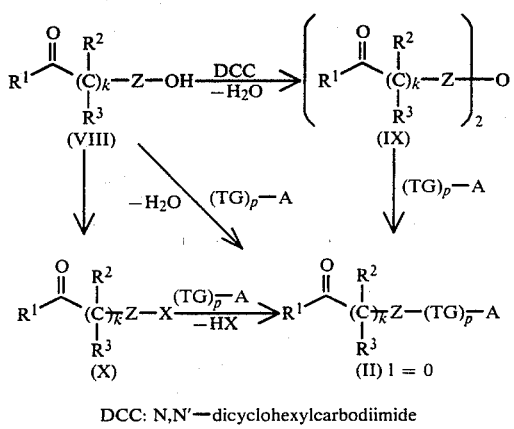

DCC: N,N'—dicyclohexylcarbodiimide

REACTION SCHEME 4

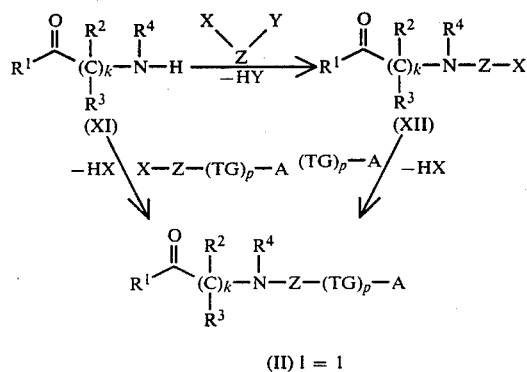

In the reaction scheme 3 and 4, A, Z, $R^1$, $R^2$, $R^3$, $R^4$, TG, k, l and p each has the same meaning as defied in formula (II), and X and Y each represents a halogen atom, an alkoxy group or a phenoxy group.

The starting materials (VIII) in Reaction Scheme 3 are readily available as commercial products or can be synthesized with reference to the methods as described, for example, in J. Dahlmann, *Chem. Ber.*, Vol. 101, page 4251 (1968); G. Le. Guillanton, *Bull. Soc. Chim. France*, page 2871 (1969); A. Takeda, *J. Org. Chem.*, Vol. 31, page 616 (1966) and *Bull. Chem. Soc. Japan*, Vol. 44, page 1342 (1971); C. A. Buehler and D. E. Pearson, *Survey of Organic Syntheses*, page 778, Wiley-Interscience (1970); S. O. Lawesson, *Acta Chem. Scand.*, Vol. 18, page 2201 (1964); H. Stetter and W. Dierichs, *Chem. Ber.*, Vol. 85, page 61 (1952); E. Berliner, *Organic Reactions*, Vol. 5, page 229 (1949); H. Hapff and T. Zimmerman, *Helv. Chim. Acta*, Vol. 47, page 1293 (1964); W. Steglich and P. Gruber, *Angew. Chem. Intern. Ed. Engl.*, Vol. 10, page 655 (1971); etc.

Also, the starting materials (XI) in Reaction Scheme 4 can be synthesized with reference to the methods as described in the following literatures, for example, G. H. Timms and E. Wildsmith, *Tetrahedron Lett.*, page 195 (1971); H. E. Baumgarten et al., *J. Amer. Chem. Soc.*, Vol. 82, page 459 and page 4422 (1960); H. E. Baumgarten and J. M. Peterson, *Organic Syntheses*, Vol. 41, page 82 (1961); M. C. Rebstock et al., *J. Amer. Chem. Soc.*, Vol. 77, page 24 (1955); N. H. Cromwell, *Chem. Rev.*, Vol. 38, page 83 (1946); P. R. Haeseler, *Organic Syntheses Coll.*, vol. 1, page 196 (1941), etc.

Specific synthesis examples of the precursor compounds according to the present invention are set forth below.

SYNTHESIS EXAMPLE 1

Synthesis of Compound (1)

23 g (0.2 mol) of levulinic acid was dissolved in 600 ml of dry ether and the solution was cooled to 0° C. with stirring. Then 100 ml of an ether solution containing 20.6 g (0.1 mol) of N,N'-dicyclohexylcarbodiimide was added dropwise over a period of 30 minutes. White colored urea was immediately formed. After the completion of the addition, the cooling bath was took off and the mixture was stirred at room temperature for 5 hours. Then the reaction mixture was cooled and the urea was removed by filtration. The filtrate was concentrated to obtain 21.5 g of levulinic anhydride as an oily product which solidified by allowing to stand. The melting point was below 30° C. The structure of the compound was determined by IR spectrum and NMR spectrum.

10.45 g (0.05 mol) of 4-hydroxymethyl-1-phenyl-5-thioxotetrazole and 10.50 g (0.1 mol) of levulinic anhydride obtained above were dissolved in 100 ml of chloroform and to the solution was added 20 ml of pyridine under cooling by an ice bath. The mixture was stirred for 1 hour while maintaining the temperature at 0° C., the ice bath was removed and the mixture was further stirred for 5 hours. The reaction mixture was poured into water and repeatedly extracted with chloroform. The organic layer thus-obtained was washed with 2N aqueous hydrochloric acid and then with water and dried with anhydrous sodium sulfate. The solvent was distilled off to obtain 16.5 g of the oily product which was separated by flash column chromatography (ethyl acetate: hexane = 1:2) to obtain 9.1 g of the desired compound, Compound (1), in the form of crystals having the melting point of 135° to 137° C.

SYNTHESIS EXAMPLE 2

Synthesis of Compound (6)

6.7 g (0.05 mol) of 5-methylbenzotriazole and 10.5 (0.1 mol) of levulinic anhydride were dissolved in 200 ml of chloroform and the solution was cooled with stirring to which was added dropwise 40 ml of pyridine. After the completion of the addition, the ice bath was removed and the mixture was further stirred at room temperature for 3 hours. The reaction mixture was poured into water and the organic layer was repeatedly washed with 2N aqueous hydrochloric acid and then with water and dried with anhydrous sodium sulfate. The solvent was concentrated to obtain 9.2 g of the crude crystals, which were recrystallized from a solvent mixture of ethyl acetate and hexane, to obtain 7.5 g of the desired compound having a melting point of 65 to 69° C.

SYNTHESIS EXAMPLE 3

Synthesis of Compound (7)

8.15 g (0.05 mol) of 5-methyl-1-hydroxymethylbenzotriazole and 10.5 g (0.1 mol) of levulinic anhydride were suspended in 10 ml of ether and to the suspension was added 20 ml of pyridine while cooling. The mixture was stirred at the same temperature as above (5° C.) for 1 hour, the ice bath was removed and the mixture was further stirred for 7 hours. The reaction mixture was poured into water and extracted with ethyl acetate. The organic layer was washed with 2N aqueous hydrochloric acid and then with water and dried with anhydrous sodium sulfate. The solvent was distilled off and 14 g of the residue was purified by flash column chromatography (benzene:ethyl acetate=4:1) to obtain 8.4 g of the desired compound having a melting point of 49° to 51° C.

SYNTHESIS EXAMPLE 4

Synthesis of Compound (10)

4 g (0.015 mol) of 1-hydroxymethyl-5-phenoxycarbonylbenzotriazole and 3.1 g (0.03 mol) of levulinic anhydride were dissolved in 20 ml of dimethylformamide and the solution was cooled to which was added 7 ml of pyridine. The ice bath was removed and the mixture was allowed to stand overnight. The reaction mixture was poured into water and extracted with ethyl acetate. The organic layer thus-obtained was washed with 2N aqueous hydrochloric acid and then with water and dried with anhydrous sodium sulfate. The solvent was distilled off and to the residue was added ether to crystallize. By recrystallization from a solvent mixture of ethyl acetate and hexane to obtain 3.8 g of the desired compound in the form of white crystals having a melting point of 116° to 120° C.

SYNTHESIS EXAMPLE 5

Synthesis of Compound (12)

13.4 g (0.05 mol) of 1,5-diphenyl-3-keto-2-pyrazolidinyl methanol and 10.5 g (0.1 mol) of levulinic anhydride were suspended in 100 ml of ether, the suspension was cooled to which was added 20 ml of pyridine and the mixture was stirred for 5 hours while maintaining the temperature as above. The reaction mixture was poured into water and extracted with ethyl acetate. The organic layer was washed with 2N aqueous hydrochloric acid and then with water and dried with anhydrous sodium sulfate. The solvent was distilled off and 19 g of the oily product thus-obtained was purified by flash column chromatography (benzene:ethyl acetate=5:1) to obtain 12 g of the desired compound as a colorless oily product.

SYNTHESIS EXAMPLE 6

Synthesis of Compound (16)

To 30 ml of a methylene chloride solution containing 4.12 g (0.020 mol) of N,N'-dicyclohexylcarbodiimide was added 30 ml of a methylene chloride solution containing 4.52 g (0.020 mol) of o-benzoylbenzoic acid under cooling with ice. Then 50 ml of a dimethylformamide solution containing 4.25 g (0.022 mol) of 5-nitro-1-hydroxymethylindazole was added dropwise thereto and the mixture was stirred for 2 hours under cooling with ice. The temperature was then gradually raised to room temperature and stirred for 12 hours. The reaction solution was concentrated under reduced pressure, the residue thus-obtained was suspended in 50 ml of ethyl acetate and the crystals were removed by filtration. The filtrate was concentrated under reduced pressure and the residue thus-obtained was recrystallized from isopropanol to obtain 5.93 g of the desired compound in the form of white crystals having a melting point of 130° to 131° C.

The precursors according to the present invention can be used in combination with two or more thereof.

The blocked photographic agents (precursors) according to the present invention may be added to any constituent layers of a silver halide photographic light-sensitive material including a silver halide emulsion layer, a coloring material layer, a subbing layer, a protective layer, an interlayer, a filter layer, an antihalation layer, an image-receiving layer, a cover sheet layer and other subsidiary layers.

Incorporation of the precursors used in the present invention into the above-described layers can be carried out by adding them to coating solutions for forming such layers as they are, or in such a state that they are dissolved in a proper concentration in such a solvent as not to affect adversely the photographic light-sensitive material, such as water, alcohol or the like. Also, the precursors can be added in such a state that they are firstly dissolved in an organic solvent having a high boiling point and/or an organic solvent having a low boiling point and then, emulsified and dispersed in an aqueous solution. Moreover, they may be added in such a state that they are loaded into polymer latexes using the methods as described in Japanese Patent Publication (unexamined) Nos. 39853/76, 59942/76 and 32552/79, U.S. Pat. No. 4,199,363, etc.

The precursors may be added at any stages of the production of the photographic light-sensitive material. However, it is generally preferable to add the precursor just before the coating.

The compounds according to the present invention can be employed, for example, in color photographic light-sensitive materials of the coupler type.

A general method for forming color images using a color photographic light-sensitive material comprises developing a silver halide light-sensitive material with an aromatic primary amine developing agent in the presence of color couplers which have such an ability as to form dyes by reacting with the oxidation products of developing agents, to produce azomethine dyes or indoaniline dyes. The basis of the above-described color development method was invented by L. D. Mannes & L. Godowsky in 1935 and thereafter, various improvements have been introduced thereinto. Nowadays, this color development method is universally employed in the art.

In this method, the substractive color process is usually employed for color reproduction, wherein silver halide emulsions which are sensitive selectively to blue, green and red lights respectively, and yellow, magenta and cyan color image-forming agents which bear their respective complementary relations to those lights are used. In order to form yellow color images, couplers of, e.g., acylacetanilide type or dibenzoylmethane type are used. In order to form magenta color images, couplers of pyrazolone type, pyrazolobenzimidazole type, cyanoacetophenone type or indazolone type are predominantly used. In order to form cyan color images, couplers of phenol type, e.g., phenols and naphthols, are predominantly used.

In general, color photographic light-sensitive materials are divided broadly into two main groups; one group consists of the coupler-in-developer type, which utilize couplers added to a developing solution, and the other group consists of those of the coupler-in-emulsion type, which contain couplers in their light-sensitive layers in such a state that the couplers may retain their own functions independently. In the latter materials, dye image-forming couplers are incorporated in silver halide emulsion layers. For couplers to be added to emulsion layers, it is necessary that they be rendered nondiffusible (diffusion resistant) in the matrix of emulsion binder.

The processing steps of color photographic light-sensitive materials of the coupler-in-emulsion type comprises basically of the following three steps.

(1) Color development step
(2) Bleaching step
(3) Fixing step

A bleaching step and a fixing step may be carried out at the same time. Such a combination is called a bleach-fixing, or blixing step, and both developed silver and undeveloped silver halide are desilvered in this step. Besides involving the above-described two basic steps, i.e., a color development step and a desilvering step, the actual processing for development processing includes auxiliary steps for the purposes of retaining photographic and physical qualities of the image, improving the storability of the image, and so on. For instance, there are steps using a hardening bath for preventing light-sensitive films from being excessively softened during the processing, a stop bath for stopping a development reaction effectively, an image-stabilizing bath for stabilizing images, a layer-removing bath for removing a backing layer from the support, and so on.

Couplers are added to or dispersed into gelatin-silver halide emulsions or hydrophilic colloid according to conventionally known methods. Specifically, a method of dispersing a coupler in the form of a mixture with an organic solvent having a high boiling point such as dibutyl phthalate, tricresyl phosphate, waxes, a higher fatty acid or its ester, etc. such a method as described in, e.g., U.S. Pat. Nos. 2,304,939 and 2,322,027 and so on; a method of dispersing a coupler in the form of a blend with an organic solvent having a low boiling point or a water soluble organic solvent; a method of dispersing a coupler in the form of a mixture with a combination of an organic solvent a high boiling point and an organic solvent having a low boiling point such a method as described in, e.g., U.S. Pat. Nos. 2,801,170, 2,801,171 and 2,949,360, and so on; a method of dispersing a coupler by itself or in combination with other couplers required for combined use, such as a colored coupler and an uncolored coupler, in the case that the coupler per se has a low melting point (e.g., not higher than 75° C.) such a method as described in German Pat. No. 1,143,707, and so on can be employed.

The photographic emulsion layers of the photographic light-sensitive materials of the present invention may contain color forming couplers, namely, compounds capable of color forming upon oxidative coupling with an aromatic primary amine developing agent (for example, phenylenediamine derivatives or aminophenol derivatives, etc.) by color development. Examples thereof include 5-pyrazolone couplers, pyrazolobenzimidazole couplers, cyanoacetylcoumarone couplers and open chain acylacetonitrile couplers, etc., as magenta couplers; acylacetamide couplers (for example, benzoylacetanilides and pivaloylacetanilides), etc., as yellow couplers; and naphthol couplers and phenol couplers, etc., as cyan couplers. These couplers are preferred to have hydrophobic groups called ballast groups in the molecule so as to be non-diffusible. The couplers may be any of 4-equivalence and 2-equivalence to silver ion. Further, they may be colored couplers having the effect of color correction or couplers which release a development inhibitor by development (the so-called DIR couplers).

In addition to DIR couplers, non-color forming DIR coupling compounds which produce a colorless product by coupling reaction and release a developing inhibitor may be incorporated.

Upon the application to the color diffusion transfer photographic process, the photographic material of the present invention may constitute any type of film unit, including a peel-apart integrated type as described in Japanese Patent Publication Nos. 16356/71 and 33697/73, Japanese Patent Publication (unexamined) No. 13040/75 and British Patent No. 1,330,524, or the peel-apart unneeded type as described in Japanese Patent Publication (unexamined) No. 119345/82.

In any film units of the above-described formats, it is advantageous to provide a polymeric acid layer protected by a neutralization timing layer from the standing of extending a latitude in the processing temperature.

Moreover, the compounds according to the present invention can be employed in black and white photographic light-sensitive materials. Suitable examples of such photographic materials include medical X-ray films for direct photography, black and white films for general photography, lithographic films, scanner films and so on.

Silver halide photographic light-sensitive materials to which the present invention can be applied do not have any particular restrictions as to, e.g., the process of preparing silver halide emulsions, halogen compositions, the crystal habit of silver halide grains, the grain size of silver halides, a chemical sensitizer, an antifoggant, a stabilizer, a gelatin hardener, a hydrophilic colloid binder, a matting agent, a dye, a sensitizing dye, a fading preventing agent, a color-mixing preventing agent, a polymer latex, a brightening agent, an antistatic agent, etc. For details of the above-described items, *Research Disclosure*, Vol. 176, pages 22 to 31 (Dec. 1978) can be, for example, referred to.

Further, there are no particular restrictions on the way to expose and the way to develop the silver halide photographic light-sensitive materials of the present invention. Known methods and known processing solutions as described, for example, in *Research Disclosure*, supra, pages 28 to 30 can be applied to the photographic materials of the present invention. The photographic processing may be either the photographic processing for forming silver images (black and white photographic processing) or that for forming dye images (color photographic processing), if desired. A processing temperature is usually selected from the range of 18° to 50° C. Of course, temperatures lower than 18° C. or those higher than 50° C. may also be employed.

Developing solutions to be employed for black and white photographic processing can contain known developing agents. Suitable examples of developing agents include dihydroxybenzenes (e.g., hydroquinone), 3-pyrazolidones (e.g., 1-phenyl-3-pyrazolidone), aminophenols (e.g., N-methyl-p-aminophenol) and so on. These developing agents may be employed independently or in combinations of two or more thereof. In addition to the developing agent, a developing solution may generally contain a known preservative, alkali agent, pH buffer, and antifoggant, and optionally, a dissolution aid, a color toning agent, a development accelerator, a surface active agent, a defoaming agent, a water softener, a hardener, a viscosity providing agent, and so on.

To the photographic emulsion of the present invention, the so-called "lithographic type" of development processing can be applied. "Lithographic type" of development processing signifies the processing in which in order to effect the photographic reproduction of line images or the photographic reproduction of halftone images by means of dots, dihydroxybenzenes are generally used as a developing agent and the development step is made to proceed infectiously under the condition that the concentration of sulfite ion is maintained at a low level.

A color developing solution is, in general, an alkaline aqueous solution containing a color developing agent.

measured, a pseudo first-order reaction rate constant ($K'$) was obtained and a half-life ($t_{\frac{1}{2}}$) was calculated. The half-life ($t_{\frac{1}{2}}$) was a time required to react a half amount of the precursor compound and calculated by the equation of $t_{\frac{1}{2}} = 0.693/k'$. Further, a half-life was determined in the same procedure as described above except that $7.2 \times 10^{-4}$ mol of sodium sulfite was previously added to the buffer and compared with that obtained from the case of without sodium sulfite whereby the release accelerating effect due to sulfite ion was evaluated. The results thus-obtained are set forth in Table 1 below.

TABLE 1

Measurement for Releasing Rate of Photographically Useful Agent
(at 25° C., buffer/acetonitrile = 1/1)

| No. | Precursor Compound | pH | $t_{\frac{1}{2}}$ (sec.) Without Na$_2$SO$_3$ | $t_{\frac{1}{2}}$ (sec.) with Na$_2$SO$_3$ | Accelerating Effect* by Addition of Na$_2$SO$_3$ |
|---|---|---|---|---|---|
| 1 | Compound (1) [Present Invention] | 10.0 | 3,600 | 237 | 15.2 |
| 2 | Compound (4) [Present Invention] | 10.0 | 2,500 | 210 | 11.9 |
| 3 | Compound (7) [Present Invention] | 10.0 | 5,400 | 439 | 12.3 |
| 4 | Compound (12) [Present Invention] | 10.0 | 7,800 | 582 | 13.4 |
| 5 | Compound (16) [Present Invention] | 10.85 | 61,900 | 7,500 | 8.25 |
| 6 | Compound (19) [Present Invention] | 10.0 | 4,500 | 417 | 10.8 |
| 7 | Compound A [Comparison] | 10.0 | 68,400 | 67,300 | 1.02 |

*calculated by $\dfrac{t_{\frac{1}{2}} \text{(without Na}_2\text{SO}_3)}{t_{\frac{1}{2}} \text{(with Na}_2\text{SO}_3)}$ Suitable examples of color developing agents which can be used include known primary aromatic amine developing agents, such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline, etc.).

After the color development processing, photographic emulsion layers are generally subjected to a bleach processing. The bleach processing may be carried out simultaneously with a fix processing, or separately therefrom. Suitable examples of bleaching agents include compounds of polyvalent metals such as iron (III), cobalt (III), chromium (VI), copper (II), etc., peroxy acids, quinones, nitroso compounds, and so on.

Now, the present invention will be illustrated in more detail with reference to the following examples, but the present invention should not be construed as being limited thereto.

EXAMPLE 1

Measurement for Releasing Rate of Photographically Useful Agent $3.6 \times 10^{-5}$ mol of the precursor compound as shown in Table 1 below was dissolved in 4 ml of acetonitrile and the solution was added to a mixture solution of 16 ml of acetonitrile and 20 ml of Britton-Robinson buffer at 25° C. The pH of the solution was adjusted to that shown in Table 1 below by means of a buffer. A definite amount of the reaction solution was picked after a definite period of time, a pH of which was adjusted to 6.25 with acetic acid and an amount of the photographically useful agent released was measured by means of high speed liquid chromatography. From the values thus- Comparison Compound A has the following structure.

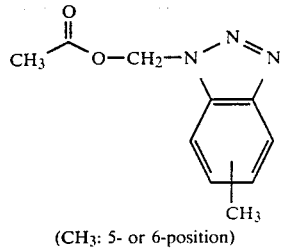

(CH$_3$: 5- or 6-position)

It is apparent from the comparison of the releasing rate of Compound (7) according to the present invention with that of Comparison Compound A that the compound according to the present invention has a rapid releasing rate in a buffer and that the releasing rate thereof is further accelerated by the addition of sulfite ion. On the contrary, the releasing rate is hardly accelerated with the comparison compound. Therefore, it can be understood that the compound according to the present invention particularly exhibits its superior feature in case of processing with a processing solution containing sulfate ions.

EXAMPLE 2

On a cellulose triacetate film support having a subbing layer was coated the emulsion layer as set forth below which was prepared by dissolving the antifoggant or antifoggant precursor as shown in Table 2 below and Magenta Coupler Cp-1 (structural formula below) in a mixture of tricresyl phosphate and ethyl acetate, emulsifying the solution into an aqueous gelatin solution and adding to a photographic emulsion to prepare Samples 1 to 7. The coated amount of each components are shown in terms of g/m² or mol/m² in parentheses below.

(1) Emulsion Layer

Negative type silver iodobromide emulsion having a particle size of 1.5μ (silver: $1.6 \times 10^{-2}$ mol/m²)

Antifoggant or precursor compound as shown in Table 2 below

Magenta Coupler Cp-1 ($1.33 \times 10^{-3}$ mol/m²)

Tricresyl phosphate (0.95 g/m²)

Gelatin (2.50 g/m²)

(2) Protective Layer 2,4-Dichloro-6-hydroxy-s-triazine sodium salt (0.05 g/m²)

Gelatin (1.30 g/m²)

These films were allowed to stand for 14 hours under the conditions of 40° C. and relative humidity of 70%. Thereafter, they were subjected to imagewise exposure for sensitometry, and then they were subjected to the following color development processing.

| Steps for Color Development Processing | Time | Temperature |
|---|---|---|
| 1. Color Development | 3'15" | 38° C. |
| 2. Bleaching | 6'30" | " |
| 3. Water Washing | 2' | " |
| 4. Fixing | 4' | " |
| 5. Water Washing | 4' | " |
| 6. Stabilizing | 1' | " |

The compositions of the processing solutions employed in the above-described color development processing steps are described below.

| Color Developing Solution: | |
|---|---|
| Water | 800 ml |
| 4-Amino-3-methyl-N—ethyl-N—(β-hydroxyethyl)aniline Sulfate | 5 g |
| Sodium Sulfite | 5 g |
| Hydroxylamine Sulfate | 2 g |
| Potassium Carbonate | 30 g |
| Potassium Hydrogencarbonate | 1.2 g |
| Potassium Bromide | 1.2 g |
| Sodium Chloride | 0.2 g |
| Trisodium Nitrilotriacetate | 1.2 g |
| Water to make | 1 liter |
| | (pH = 10.1) |
| Bleaching Solution: | |
| Water | 800 ml |
| Ammonium Ferric Ethylenediaminetetraacetate | 100 g |
| Disodium Ethylenediaminetetraacetate | 10 g |
| Potassium Bromide | 150 g |
| Acetic Acid | 10 g |
| Water to make | 1 liter |
| | (pH = 6.0) |
| Fixing Solution: | |
| Water | 800 ml |
| Ammonium Thiosulfate | 150 g |
| Sodium Sulfite | 10 g |
| Sodium Hydrogensulfite | 2.5 g |
| Water to make | 1 liter |
| | (pH = 6.0) |
| Stabilizing Solution: | |
| Water | 800 ml |
| Formaline (37%) | 5 ml |
| Driwel (trade name surface active agent, made by Fuji Photo Film Co., Ltd.) | 3 ml |
| Water to make | 1 liter |

The photographic properties thus-obtained are shown in Table 2 below.

TABLE 2

| Sample | Antifoggant or Precursor Compound | Amount Added (mol/m²) | Fog | Gamma | Relative* Sensitivity | Maximum Color Density |
|---|---|---|---|---|---|---|
| 1 | None [Control] | — | 0.15 | 0.71 | 100 | 1.63 |
| 2 | Compound (1) [Present Invention] | $2.0 \times 10^{-6}$ | 0.09 | 0.66 | 95 | 1.50 |
| 3 | Compound (3) [Present Invention] | $2.0 \times 10^{-6}$ | 0.08 | 0.65 | 92 | 1.47 |
| 4 | Compound (7) [Present Invention] | $2.0 \times 10^{-5}$ | 0.11 0.69 | | 98 | 1.55 |
| 5 | Precursor A [Comparison] | $2.0 \times 10^{-5}$ | 0.15 | 0.70 | 98 | 1.59 |
| 6 | Antifoggant B [Comparison] | $2.0 \times 10^{-6}$ | 0.05 | 0.38 | 23 | 0.95 |
| 7 | Antifoggant C [Comparison] | $2.0 \times 10^{-5}$ | 0.09 | 0.53 | 47 | 1.20 |

*Relative sensitivity is shown by a reciprocal of an exposure amount required for obtaining a color density of fog + 0.2 and being taken the sensitivity of Control Sample 1 as 100.

The compounds for comparison and the coupler employed in the above-described samples are set forth below.

Precursor A for comparison:

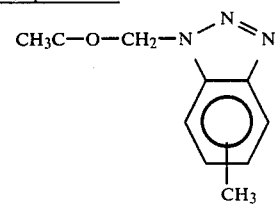

(CH₃: 5- or 6-position)

Antifoggant B for comparison

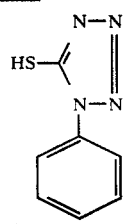

Antifoggant C for comparison:

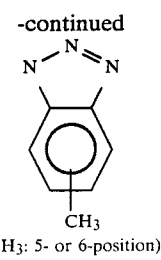

(CH₃: 5- or 6-position)

Magenta Coupler Cp-1

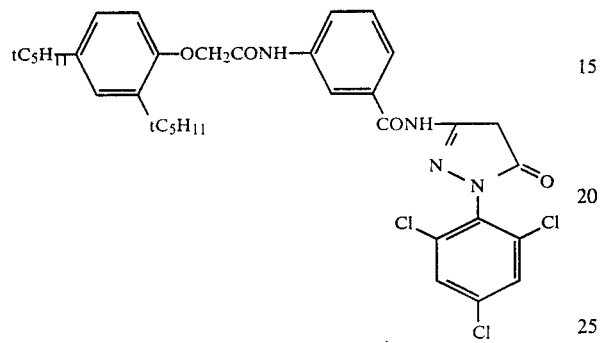

From the photographic properties shown in Table 2 about it is apparent that Samples 2 to 4 wherein the precursor compounds according to the present invention are used can depress the fog without accompanying substantial decrease in the sensitivity.

EXAMPLE 3

On a cellulose triacetate film support having a subbing layer there was coated an emulsion layer as set forth below, which was prepared by dissolving the pyrazolidone or precursor thereof in tricresyl phosphate together with Magenta Coupler Cp-1, emulsifying, and adding to a photographic emulsion as describes below to prepare Samples 8 to 13. The coated amounts of each components are shown in terms of g/m² or mol/m² in parentheses below.

(1) Emulsion Layer
Negative type silver iodobromide emulsion having a particle size of 1.5μ (silver: $1.6 \times 10^{-2}$ mol/m²)
Magenta Coupler Cp-1 ($1.33 \times 10^{-3}$ mol/m²)
Pyrazolidone or precursor thereof as shown in Table 3 below ($1.50 \times 10^{-3}$ mol/m²)
Gelatin (2.50 g/m²)

(2) Protective Layer
Gelatin (1.30 g/m²)
2,4-Dichloro-6-hydroxy-s-triazine sodium salt (0.05 g/m²)

These films were allowed to stand for 14 hours under the conditions of 40° C. and relative humidity of 70% and then subjected to imagewise exposure for sensitometry and color development processing as described in Example 2. The photographic properties thus-obtained are shown in Table 3 below.

TABLE 3

| Sample | Pyrazolidone or Precursor thereof | Fog | Gamma | Relative Sensitivity | Maximum Color Density |
|---|---|---|---|---|---|
| 8 | None [Control] | 0.1 | 0.68 | 100 | 1.62 |
| 9 | Compound (12) [Present Invention] | 0.14 | 0.73 | 123 | 1.72 |
| 10 | Compound (13) [Present Invention] | 0.15 | 0.78 | 115 | 1.72 |
| 11 | Compound (21) [Present Invention] | 0.14 | 0.72 | 112 | 1.70 |
| 12 | Pyrazolidone D [Comparison] | 0.26 | 0.93 | 78 | 1.78 |
| 13 | Pyrazolidone E [Comparison] | 0.18 | 0.89 | 92 | 1.75 |

The pyrazolidones for comparison used in the above-described samples are set forth below.

Pyrazolidone D　　　　Pyrazolidone E

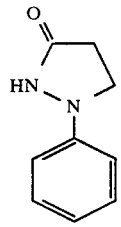 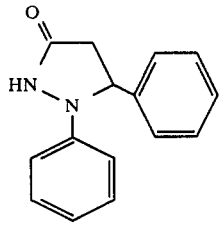

From the results shown in Table 3 above, it is apparent that Samples 9 to 11 wherein the compounds according to the present invention are used exhibit increase in sensitivity without any substantial increase in fog, while increases in fog and desensitization are observed in the comparative samples to which the auxiliary developing agents D and E were added.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material which comprises a support having thereon a light-sensitive silver halide emulsion layer, wherein the photographic light-sensitive material therein contains a blocked photographic agent capable of releasing a photographically useful agent, wherein the blocked photographic agent is a compound represented by formula (I):

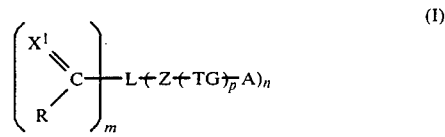

wherein $X^1$ represents an oxygen atom or a sulfur atom; Z represents an electrophilic group; A represents a photographically useful agent moiety; TG represents a timing group; L represents a linking group which is bonded to

through a carbon atom thereof and L is capable of forming a 5-membered to 7-membered ring upon a nucleophilic attack of the oxygen atom or sulfur atom represented by $X^1$ on the electrophilic group represented by Z, said linking group being selected from the group consisting of an alkylene group, an alkyloxyalkylene group, an alkylaminoalkylene group, an alkenylene group, an arylene group, a cyclocyclene group, a heterocyclene group, an alkyleneamino group, an alkenyleneamino group, an aryleneamino group, a cyclocycleneamino group, a heterocycleneamino group and combinations thereof; R represents a hydrogen atom or a substituent which is bonded through a carbon atom thereof; m and n each is an integer of from 1 to 3; and p is 0 or 1.

2. A silver halide photographic light-sensitive material as in claim 1, wherein the photographically useful group contains a timing group.

3. A silver halide photographic light-sensitive material as in claim 1, wherein the photographic material is a silver halide color photographic light-sensitive material containing a color forming coupler.

4. A silver halide photographic light-sensitive material as in claim 1, wherein m and n each is 1 or 2.

5. A silver halide photographic light-sensitive material as in claim 1, wherein the photographically useful agent in the moiety represented by A is an antifoggant, a development restrainer, a developing agent, an auxiliary developing agent, a development accelerator, a fogging agent, a dye or a redox compound capable of releasing a photographically useful agent as a function of silver halide development.

6. A silver halide photographic light-sensitive material as in claim 5, wherein the photographically useful agent is selected from mercaptotetrazoles, mercaptotriazoles, mercaptobenzimidazoles, benzotriazoles, benzimidazoles and indazoles.

7. A silver halide photographic light-sensitive material as in claim 5, wherein the photographically useful agent is selected from p-phenylenediamines, hydroquinones and aminophenols.

8. A silver halide photographic light-sensitive material as in claim 5, wherein the photographically useful agent is selected from pyrazolidones.

9. A silver halide photographic light-sensitive material as in claim 5, wherein the photographically useful agent is selected from hydrazines, hydrazides, acetylenic compound and tetrazolium salts.

10. A silver halide photographic light-sensitive material as in claim 5, wherein the photographically useful agent is selected from azo compounds.

11. A silver halide photographic light-sensitive material as in claim 1, wherein the photographically useful agent in the moiety represented by A is a compound having a redox function so as to enable the release of photographically useful agent as a function of silver halide development.

12. A silver halide photographic light-sensitive material as in claim 11, wherein the photographically useful agent in the moiety represented by A is a coloring material for color diffusion transfer or a development inhibitor releasing hydroquinone.

13. A silver halide photographic light-sensitive material as in claim 1, wherein p is 0.

14. A silver halide photographic light-sensitive material as in claim 1, wherein p is 1.

15. A silver halide photographic light-sensitive material as in claim 14, wherein the timing group TG is a connecting group selected from a group which releases the photographically useful agent by an intramolecular ringclosing reaction, a group which releases the photographically useful agent through intramolecular electron transfer, a group which releases the photographically useful agent with the evolution of carbon dioxide, or a group which releases the photographically useful agent with the evolution of formaldehyde.

16. A silver halide photographic light-sensitive material as in claim 15, wherein the timing group TG is a group represented by the formula

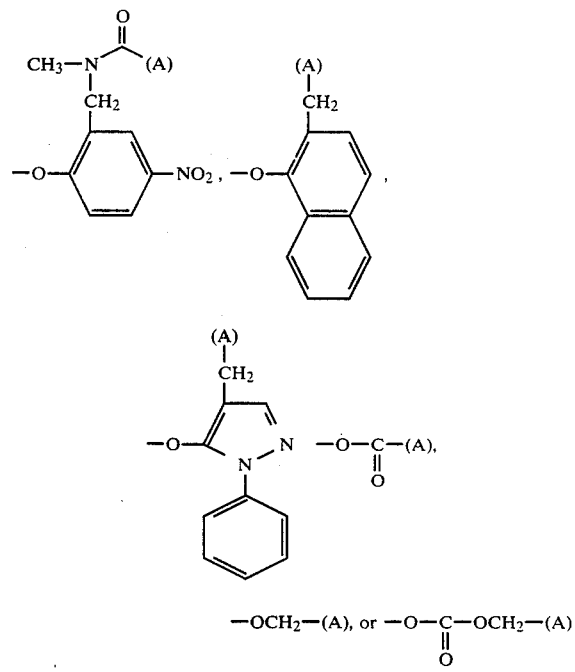

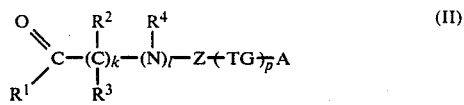

wherein A represents a photographically useful agent moiety.

17. A silver halide photographic light-sensitive material as in claim 1, wherein the electrophilic group represented by Z is a carbonyl group, a thiocarbonyl group, a sulfonyl group, a sulfinyl group, an allyl group or a benzyl group.

18. A silver halide photographic light-sensitive material as in claim 1, wherein the photographic material is a color diffusion transfer silver halide photographic light-sensitive material containing a dye-image providing material.

19. A silver halide photographic light-sensitive material as in claim 1, wherein the photographic material is a black and white silver halide photographic light-sensitive material which forms a silver image upon black and white development.

20. A silver halide photographic light-sensitive material as in claim 1, wherein the substituent which is bonded through a carbon atom represented by R is an alkyl group, an alkenyl group, an aryl group, a cycloalkyl group, or a heterocyclic group.

21. A silver halide photographic light-sensitive material as in claim 1, wherein the blocked photographic agent is a compound represented by formula (II):

$$\underset{R^1}{\overset{O}{\underset{\|}{C}}}-(C)_k-(N)_l-Z+TG\!\!+\!_p\!A \quad (II)$$
$$\quad\quad\; R^3$$

(with $R^2$, $R^4$ on the C and N)

wherein A, TG, p, and Z each has the same meaning as defined therefor in formula (I); $R^1$ has the same meaning as defined for R in formula (I), $R^2$ and $R^3$, which may be the same or different, each represents a hydrogen atom, a halogen atom, an alkyl group, an alkenyl group, a phenyl group, a hydroxy group, an alkoxy group, or an acyl group, each of these groups may have a substituent or $R^2$ and $R^3$ together form a double bond or a ring; $R^4$ represents an alkyl group, an alkenyl group, or a phenyl group; k is an integer from 1 to 4; l is 0 or 1; and the sum of k and l is from 2 to 4.

22. A silver halide photographic light-sensitive material as in claim 21, wherein k is 2, 3, or 4 and the carbon atom substituted with $R^2$ and $R^3$ forms a cycloalkyl ring, an aromatic ring or a heterocyclic ring.

23. A silver halide photographic light-sensitive material as in claim 21, wherein $R^1$ represents a hydrogen atom, an alkyl group having from 1 to 17 carbon atoms, an alkenyl group having from 3 to 17 carbon atoms, a phenyl group having from 6 to 21 carbon atoms, or a heterocyclic group having from 4 to 21 carbon atoms.

24. A silver halide photographic light-sensitive material as in claim 21, wherein $R^2$ and $R^3$ each represents a hydrogen atom, a halogen atom, or an alkyl group.

25. A silver halide photographic light-sensitive material as in claim 22, wherein the ring which is formed with the carbon atom substituted with $R^2$ and $R^3$ is a benzene ring.

26. A silver halide photographic light-sensitive material as in claim 21, wherein k is 2 or 3 and each of

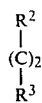

or

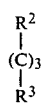

has the same structure.

27. A silver halide photographic light-sensitive material as in claim 21, wherein k is 2 or 3 and each of

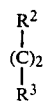

or

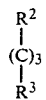

has a different structure.

28. A silver halide photographic light-sensitive material as in claim 21, wherein $R^4$ represents an alkyl group having from 1 to 18 carbon atoms or a phenyl group having from 6 to 21 carbon atoms.

29. A silver halide photographic light-sensitive material as in claim 21, wherein Z represents a carbonyl group or a sulfonyl group.

30. A silver halide photographic light-sensitive material as in claim 21, wherein k is 1, 2 or 3.

31. A silver halide photographic light-sensitive material as in claim 30, wherein k is 1 and l is 1, k is 2 and l is 0 or 1, or k is 3 and l is 0.

32. A silver halide photographic light-sensitive material as in claim 21, wherein the photographically useful agent in the moiety represented by A is an antifoggant, a developing agent, or an auxiliary developing agent.

33. A silver halide photographic light-sensitive material as in claim 1, wherein the blocked photographic agent is present in a silver halide emulsion layer.

34. A silver halide photographic light-sensitive material as in claim 1, wherein the blocked photographic agent is an antifoggant of mercapto group-containing type and the blocked photographic agent is contained in the photographic material in an amount of $10^{-9}$ to $10^{-2}$ mole per mole of silver in the silver halide emulsion.

35. A silver halide photographic light-sensitive material as in claim 1, wherein the blocked photographic agent is an antifoggant of azole type and the blocked photographic agent is contained in the photographic material in an amount of $10^{-8}$ mole per mole of silver in the silver halide emulsion.

36. A silver halide photographic light-sensitive material as in claim 1, wherein the blocked photographic agent is a developing agent of p-phenylenediamine type or an auxiliary developing agent of pyrazolidone type and the blocked photographic agent is contained in the photographic material in an amount of $10^{-4}$ to 10 mole per mole of silver in the silver halide emulsion.

* * * * *

UNITED STATES PATENT AND TRADEMARK OFFICE
CERTIFICATE OF CORRECTION

PATENT NO. : 4,554,243
DATED : November 19, 1985
INVENTOR(S) : Mitsunori Ono; Isamu Itoh It is certified that error appears in the above-identified patent and that said Letters Patent is hereby corrected as shown below:

On the title page, in field [75], after "Itoh" insert the following

-- ; Akihiko Ikegawa; and Keiji Mihayashi --; delete "both" and insert therefor -- all --.

Signed and Sealed this

Eighth Day of September, 1992

Attest:

DOUGLAS B. COMER

*Attesting Officer*    *Acting Commissioner of Patents and Trademarks*